United States Patent [19]

De Pasquale et al.

[11] Patent Number: 4,579,966

[45] Date of Patent: Apr. 1, 1986

[54] TERPENOID SILANES

[75] Inventors: Ralph J. De Pasquale, Jacksonville; Paul W. Kremer, Gainesville, both of Fla.

[73] Assignee: SCM Corporation, New York, N.Y.

[21] Appl. No.: 691,405

[22] Filed: Jan. 14, 1985

[51] Int. Cl.$^4$ ............................. C07F 7/08; C07F 7/18
[52] U.S. Cl. .................................... 556/482; 556/465; 556/489
[58] Field of Search ................. 556/465, 482, 489

[56] References Cited

U.S. PATENT DOCUMENTS 3,215,719  11/1965  Allen et al. ........................ 556/482
4,500,725   2/1985  Yemoto et al. ................... 556/482

Primary Examiner—Paul F. Shaver
Attorney, Agent, or Firm—R. A. Sturges; T. M. Schmitz

[57] ABSTRACT

Novel terpenoid alkoxysilanes having the general formula:

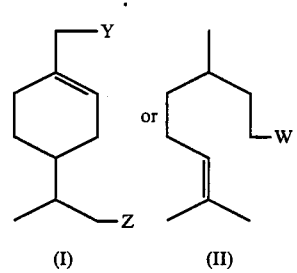

(I)    (II)

wherein Y is hydrogen or $Si(R^2)_nX_m(OR^3)_{3-(n-m)}$, Z is hydrogen or $Si(R^2)_nX_m(OR^3)_{3-(n+m)}$, one of Y and Z being $Si(R^2)_nX_m(OR^3)_{3-(n+m)}$, $R^2$ and $R^3$ being the same or different $C_1$-$C_3$ alkyl group, X is halogen, m and n are independently selected from 1 and 0, and II W is $Si(R^2)_nX_m(OR^3)_{3-(n+m)}$, where $R^2$, $R^3$, X, n and m are as defined above.

10 Claims, No Drawings

TERPENOID SILANES

This invention relates to silanes and more particularly alkylene substituted silanes in which the alkylene group directly attached to silicon is derived from a terpenoid hydrocarbon.

BACKGROUND OF THE INVENTION AND PRIOR ART

Functional and non-functional substituted alkyl silanes are known to the art for their bonding ability to a variety of inorganic/mineral matrices including glass, silica, aluminum trihydrate, clays, talc, titanium dioxide, etc., as well as certain metals/metaloids like aluminum, titanium, silicon, iron, copper, zinc, etc. Alkoxysilane treatment of a mineral affects surface properties converting an initially hydrophilic to a hydrophobic-organophilic material. Applications have been based on this phenomenon. For example, masonry is waterproofed and resists halide ion intrusion when finished with an alkoxysilane (See U.S. Pat. No. 3,772,065 to Seiler; U.S. Pat. No. 4,342,796 to Brown et al). Minerals when pretreated with alkoxy-silanes are made compatible with organic polymers increasing wet-out and decreasing viscosity of the mix. Composites derived from mineral filled or reinforced thermosets, thermoplastics or elastomers show improved performance properties, in particular resistance to aging in humid environments, when a functional alkyl alkoxysilane is used to either precoat the mineral or as an integral component composites that have shown property improvement by functional alkyl silane additives include polyesters-saturated and unsaturated, EPDM, SBR, polyisoprene, phenolics, epoxies, polyolefins, polyamides, polyimides, polyurethanes, acrylics, alkyds, PVC, and the like.

Terpenes are naturally occurring isoprene homologs that enjoy commercialization as intermediates (vitamins and insecticides), aroma and flavor components, disinfectants, cleaning compounds, catalysts, inhibitors and the like. In contrast to petroleum based chemicals, terpenoids, derived from natural sources (plants-pines and animals) are a renewable resource that contain an abundance of both unsaturation and chirality.

This invention describes certain terpenoid silanes resulting in novel compositions that show significant utility in the chemical industry in the uses described above.

The present invention provides certain novel silane derivatives of terpenoid hydrocarbons, particularly limonene and pinene to yield chiral derivatives, which compounds are useful as waterproofing materials when applied to concrete driving surfaces in the manner indicated in the aforesaid U.S. Pat. No. 4,342,796.

BRIEF STATEMENT OF THE INVENTION

Briefly stated, the present invention is a terpenoid silane having the general formula:

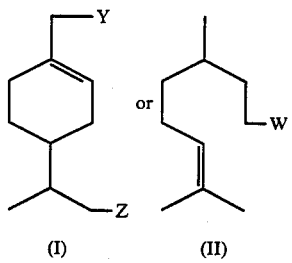

(I)     (II)

wherein I, Y is hydrogen or $Si(R^2)_n X_m (OR^3)_{3-(n+m)}$, Z is hydrogen or $Si(R^2)_n X_m (OR^3)_{3-(n+m)}$, $R^2$ and $R^3$ being the same or different $C_1$–$C_3$ alkyl groups, X is halogen, or analogous hydrolytically labile group (amine oximino, etc.) n is selected from 1 and 0, m is 0, 1, 2 or 3, or II, W is $Si(R^2)_n X_m (OR^3)_{3-(n+m)}$, $R^2$, $R^3$, X, m and n being as defined above.

DETAILED DESCRIPTION OF THE INVENTION AND SPECIFIC EXAMPLES

As indicated above, the novel compounds of the present invention are derivatives of terpeneoid hydrocarbons, as distinct from petroleum hydrocarbons. The materials are characterized by unsaturation located in a structure containing 10 skeletal carbon atoms. The starting terpenoid material may be mono- or di-unsaturated, conjugated or nonconjugated and is characterized by a chiral structure. Surprisingly, in the course of reaction with a silylating agent, this chirality is preserved. Triply unsaturated terpenes, such as myrcene, are achiral. Moreover, petroleum derived unsaturates are racemic. The silylating reaction is largely regiospecific and occurs at the least substituted double bond. Polysilylation does not occur. The products are useful as waterproofing agents for masonry and concrete and may be used for those purposes in known manners.

Typical examples of terpenoid hydrocarbons which may be used include alpha-pinene, beta-pinene, limonene, d-limonene, l-limonene, isolimonene, camphene, gamma-fenchene, delta-fenchene, beta-fenchene, epsilon-fenchene, alpha-fenchene, beta-phellandrene, alpha-phellandrene, verbenene, Delta-3,8-p-menthadiene, Delta-2,8-p-menthadiene, terpinolene, gamma-terpinene, alpha-terpinene, etc.

Silylation is most conveniently effected with silylating agent having the general formula

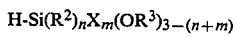

$$H-Si(R^2)_n X_m (OR^3)_{3-(n+m)}$$

wherein $R^2$, $R^3$, X and the integers m and n have the meanings given above. For most purposes, however, the trialkoxy silanes, the mono/alkyl dialkoxy silanes and the trihalo silanes are preferred.

It becomes convenient to illustrate the present invention by specific examples, it being understood that these examples are for illustrative purposes only and not be be construed as limiting the scope of the invention.

EXAMPLE I

4R-9-Triethoxysilylmenthene-1

Platinum on carbon (Pt/C) (5%, 1 g) was placed in a flask in an inert atmosphere, then d-limonene (68 g, 0.5 mole) was added and the mixture stirred and heated at 80 degrees C. Triethoxysilane (82 g, 0.5 mole) was added dropwise to the mixture over a 2 hour period.

The mixture was allowed to stir at temperature, monitored by gas liquid chromatography, (GLC), and cooled to ambient temperature when the limonene conversion reached 65% (ca. 16 hours). Selectivity exceeded 90%. The product, isolated by filtration and distillation, b.p. 128 degrees/1 mm, was a clear mobile liquid with a 15.23 min retention time by GLC analysis on 3% SP 2100 (Silicone Products) on Supelcoport (a mineral matrix, silica-alumina) from a 50 degrees–200 degrees program at 16 degrees/min.

The following spectroscopic characteristics are consistent with the structure for 4R-9-Triethoxysilylmenthene-1: NMR (CDCl$_3$) 0.8 (d of d, 2), 0.95 (d, 2), 1.2 (t, 9), 1.4 to 2.0 (b, 12), 3.8 (q, 6), 5.3 (bs, 1) ppm; Ir (neat) 1770, 1420, 1380, 1180–1150, 950, 775 cm$^{-1}$, (alpha)$_d^{20}$ 45.8° (neat).

EXAMPLE II

4R-9-Methyldiethoxysilylmenthene-1

In an inert atmosphere, d-limonene (60 g, 0.44 mole) is added to 5% Pt/C (1.0 g) and the stirred mixture heated to 90 degrees when methyl diethoxysilane (63.5 g, 0.47 mole) is added dropwise. At the completion of the addition (slightly exothermic), the reaction mixture is heated for 16 hours at 95 degrees to affect a 65% conversion by GLC. Fifty-four grams of product was isolated by filtration followed by distillation, b.p., 138–142 degrees/3 mm in a 70% yield. NMR (CDCl$_3$): 0.1 (s, 3), 0.7 (d of d, 2), 0.9 (d, 2), 1.1 (t, 6), 1.4–2.1 (b, 12), 3.7 (q, 4), 5.3 (bs, 1) ppm; mass spectrum: m/e (70 ev) 270 (m+).

EXAMPLE III

4S-7-Trimethoxysilylmenthene-1

2,2′-azobis(2-methyl)-propionitrile (Reg. No. 78-67-1) (2 g) then trichlorosilane (150 g, 1.1 mole) were added to (−)-beta-pinene (125 g, 0.919 mole) in an autoclave which was sealed, heated, and stirred at 150 degrees C. (pressure max 200 psig) for 1 hour. The cooled mixture was vented and analyzed by GLC (3% SP 2100 column) showing 61% pinene conversion. The material was topped by distillation leaving 144 g (58%) of crude 4S-7-trichlorosilylmenthene-1 which was used directly in the next step.

124 g, 0.46 mole of 4S-7-trichlorosilylmenthene-1 were placed in a flask and treated with trimethylorthoformate (150 g, 1.4 mole)/methanol (32 g, 1.0 mole) solution dropwise at such a rate to avoid internal temperature exceeding 30 degrees. At the completion of the addition, the solution was heated at 80 degrees for two hours. At this time, a sample was withdrawn for potentiometric chloride analysis which was 0.01%. the titled compound was purified by fractional distillation b.p. 80–85 degrees/1 mm affording 98 g (81%) of a clear fluid liquid. Mass spectrum (70 ev) showed peaks at m/e 258 (m+) and 227 (m+−31) while the NMR (CDCl$_3$) showed absorptions at 0.85 (d, 6), 1.5–2.1 (bm, 10), 3.51 (s, 9) and 5.2–5.4 (bs, 1) ppm; (alpha)$_d^{20}$—5.6° (neat) The spectroscopic data are consistent with the assigned structure.

A 10′×⅛″ stainless steel gas chromatograph column is made by the standard method using 4S-7-trimethoxysilylmenthene-1 as the chiral liquid phase (10%) on chromasorb P (40 mesh). Analysis of 0.5 microliter sample of ±beta-pinene shows an incompletely resolved doublet centered at 7 minutes retention time on a Varian 1400 Aerograph chromatograph (T. C. detector) operating at 80 degrees isothermally (150 degrees injection port) with a 30 cc/minute helium flow rate. Control analysis under similar conditions with a carbowax or SP2100 (liquid phase) column fails to show diastereomeric pinene separation. Achiral silanes as liquid phase do not effect such a separation.

EXAMPLE IV

3S-Citronellyldimethylethoxysilane

3S-Dihydromyrcene (50 g, 0.36 mole), dimethylethoxysilane (48.9 g, 0.47 mole) and 1 ml of a 1% acetone solution of chloroplatinic acid hexahydrate are stirred and heated together from reflux temperature to 60 degrees C., for 16 hours. At this time, GLC shows 80% starting material conversion. Distillation affords 51.8 g (75%) of titled compound b.p. 128–130 degrees/5 mm. NMR (CDCl$_3$) 0.05 (s, 6), 0.45–0.7 (m, 2), 0.88 (bd, 3), 1.1 (t, 3), 1.35 (bm, 5) 1.62 (s, 3), 1.68 (s, 3), 1.9–2.1 (bm, 2), 3.8 (q, 2) and 5.1 (bt, 1) ppm; mass spectrum: m/e (70 ev) 242 (m+).

EXAMPLE V

3S-Citronellyltriethoxysilane

Triethoxysilane (60 g, 0.37 mole) was added to a solution of 3S-dihydromyrcene (3,7-dimethyl-1,7-octadiene) (50 g, 0.36 mole) and 1 ml of 1% chloroplatinic acid hexahydrate in acetone. The resultant solution was heated with stirring at 60 degrees for 8 hours. GLC of the cooled reaction mixture showed 75% conversion of reactants to a dominant product. Titled compound was isolated by distillation, b.p. 140 degrees/5 mm (65 g, 78% yield). NMR (CDCl$_3$): 0.5–0.8 (m, 2), 0.9 (bd, 3), 1.2 (t, 9), 1.3 (bm, 5), 1.62 (s, 3) 1.7 (s, 3), 1.92–2.2 (bm, 2), 3.85 (q, 6), and 5.2 (bt, 1) ppm; mass spectrum: m/e (70 ev) 302 (m+).

Similar results are obtained using other mono- or di-ethylenically unsaturated terpene hydrocarbons such as alpha-pinene, 1-menthene, camphene, a-fenchene, phellandrene, verbenene, terpinolene, alpha-terpinene, delta-terpinene, p-menthadiene, etc.

The utility of these compounds as viscosity control agents and waterproofing agents is illustrated in the following examples:

EXAMPLE VI

Natural rubber (25% solids in toluene) having a 44,000 centipoise viscosity (Brookfield, 22.4 degrees C.) was thoroughly mixed at 10% loading level with "Suprex" (Huber Company) hydrous clay. The blend viscosity was 77,200 centipoise (22.8 degrees C.). Similar viscosity of a blend prepared from hydrous clay surface treated with 1% vinyltriethoxysilane was unchanged within experimental error. Pretreatment of the hydrous clay with 1% 3S-citronellyl-triethoxysilane effects a 15% viscosity reduction of the resulting treated clay-natural rubber blend.

EXAMPLE VII

Four inch Portland cement concrete cubes were fabricated, lightly sandblasted and dried in a vacuum oven (125 degrees, 50 mm, 24 hours) then allowed to cool to ambient. A cube surface was treated to wetness with a 40% methyl ethyl ketone solution of an alkoxysilane in two applications and air dried (15 minutes) after each application. The block was then oven baked at 70 degrees/24 hours. The cured, treated cube was immersed in water, withdrawn every 24 hours, shaken to remove surface droplets, weighed, and returned to the water bath. The experiment continued for 10 days. First order water absorption rate constants (±10%) derived from particular silanes are 0.38 (4R-9-triethoxysilylmenthene-1), 0.48 (ethyltriethoxysilane) and 0.60 (control, methyl ethyl ketone solvent, no silane) days⁻1.

What is claimed is:

1. A terpenoid silane having the general formula

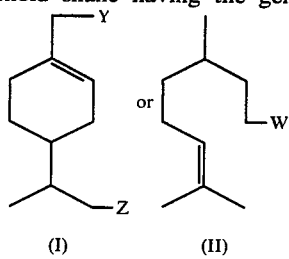

(I)   (II)

wherein Y is H or $-Si(R^2)_nX_m(OR^3)_{3-(n+m)}$, Z is H or $Si(R^2)_nX_m(OR^3)$, one of Y and Z being $Si(R^2)_nX_m(OR^3)_{3-(n+m)}$, $R^2$ and $R^3$ being the same or different lower alkyl, X is halogen, n is 0 or 1 and m is selected from 0, 1, 2, or 3, or II, W is $Si(R^2)_nX_m(OR^3)_{3-(n+m)}$ wherein $R^2$, $R^3$, X, n and m are as defined above.

2. 4S-7-trialkoxysilylmenthene-1.
3. 4S-7-trimethoxysilylmenthene-1.
4. 4S-7-triethoxysilylmenthene-1.
5. 4R-9-trialkoxysilylmenthene-1.
6. 4R-9-trimethoxysilylmenthene-1.
7. 4R-9-triethoxysilylmenthene-1.
8. 4R-9-methyldiethoxysilylmenthene-1.
9. 3S-Citronellyldimethylethoxysilane.
10. 3S-Citronellyltriethoxysilane.

* * * * *